(12) United States Patent
Oh et al.

(10) Patent No.: US 9,174,925 B2
(45) Date of Patent: Nov. 3, 2015

(54) PHORBOL TYPE DITERPENE COMPOUND, PHARMACEUTICAL COMPOSITION FOR TREATMENT OR PREVENTION OF VIRAL INFECTIOUS DISEASES INCLUDING SAME

(71) Applicant: KOREA RESEARCH INSTITUTE OF BIOSCIENCE AND BIOTECHNOLOGY, Daejeon (KR)

(72) Inventors: Sei Ryang Oh, Daejeon (KR); Jae Wha Kim, Daejeon (KR); Yi Hua Pei, Daejeon (KR); Hyeong Kyu Lee, Daejeon (KR); Ho Bum Kang, Daejeon (KR); Doo Young Kim, Daejeong (KR); Kyung Seop Ahn, Daejeon (KR); Da Chung Ji, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 15 days.

(21) Appl. No.: 14/353,892

(22) PCT Filed: Sep. 28, 2012

(86) PCT No.: PCT/KR2012/007896
§ 371 (c)(1),
(2) Date: Aug. 4, 2014

(87) PCT Pub. No.: WO2013/062247
PCT Pub. Date: May 2, 2013

(65) Prior Publication Data
US 2014/0364492 A1 Dec. 11, 2014

(30) Foreign Application Priority Data
Oct. 26, 2011 (KR) .................. 10-2011-0110184

(51) Int. Cl.
| C07C 69/21 | (2006.01) |
| C07C 69/753 | (2006.01) |
| C07C 69/33 | (2006.01) |
| A23L 1/29 | (2006.01) |
| A61K 31/215 | (2006.01) |

(52) U.S. Cl.
CPC ............. *C07C 69/753* (2013.01); *A23L 1/29* (2013.01); *A61K 31/215* (2013.01); *C07C 69/33* (2013.01); *A23V 2002/00* (2013.01); *C07C 2103/40* (2013.01)

(58) Field of Classification Search
None
See application file for complete search history.

(56) References Cited

U.S. PATENT DOCUMENTS
4,460,685 A 7/1984 Vilcek et al.

FOREIGN PATENT DOCUMENTS
| JP | H08-310993 A | 11/1996 |
| JP | H10-287617 A | 10/1998 |
| KR | 10-2011-0049722 A | 5/2011 |

*Primary Examiner* — Yevegeny Valenrod
(74) *Attorney, Agent, or Firm* — Masuvalley & Partners (57) ABSTRACT

The present invention relates to a diterpene compound derived from *Aleurites fordii*, and a pharmaceutical composition for treating or preventing viral infectious diseases, a health functional food for preventing or ameliorating viral infectious diseases and a composition for enhancing the production of interferon-gamma, which comprise the diterpene compound. Furthermore, the present invention relates to a method for preventing or treating viral infectious diseases including administering the composition to a subject having a viral infectious disease occurrence or a risk thereof with a therapeutically effective dose.

3 Claims, 8 Drawing Sheets

PHORBOL TYPE DITERPENE COMPOUND, PHARMACEUTICAL COMPOSITION FOR TREATMENT OR PREVENTION OF VIRAL INFECTIOUS DISEASES INCLUDING SAME

This application is a national phase application under 35 U.S.C. §371 of International Application Serial No. PCT/KR2012/007896 filed on Sep. 28, 2012, and claims the priority under 35 U.S.C. §119 to Korean Patent Application No. 10-2011-0110184, filed on Oct. 26, 2011, which are hereby expressly incorporated by reference in their entirety for all purposes.

TECHNICAL FIELD

The present invention relates to a diterpene compound derived from *Aleurites fordii*, and a pharmaceutical composition for treating or preventing viral infectious diseases, a health functional food for preventing or ameliorating viral infectious diseases and a composition for enhancing the production of interferon-gamma, which comprise the diterpene compound. Furthermore, the present invention relates to a method for preventing or treating viral infectious diseases including administering the composition to a subject having a viral infectious disease occurrence or a risk thereof with a therapeutically effective dose.

BACKGROUND ART

The production of interferon-γ(IFN-γ) in immunocytes is an important step in early-stage self-defense and tumor control against virus and bacterial infection (Biron, C. A. et al., *Annu. Rev. Immunol.* 1999, 17, 189-220). IFN-γ is produced in natural killer (NK) and natural killer T (NKT) cells that are generally used as effector cells in regulating immune reactions (Schoenborn, J. R. et al., *Adv. Immunol.* 2007, 96, 41-101). IFN-γ expression is particularly related to a pro-inflammatory state. The biological role of cytokain IFN-γ in a defense system is well known, and the role is related to both virus replication and direct suppression of immunostimulation (Gessani, S. et al., *Cytokine & Growth F. R.* 1998, 9, 117-123; Goodbourn, S. et al., *J. Gen. Virol.* 2000, 81, 2341-2364).

Pharmaceutical markets have grown globally due to an increase in incomes, aging population, increased demand for chronic disease-related medicines, life expectancy increase and the like, and as a result, research and development on biopharmaceuticals have increased in pharmaceutical industries at home and abroad. Among other things, there has been increased demand for antiviral therapeutic agent-related research that is the base of the development of AIDS therapeutic agents, and liver disease and influenza disease therapeutic agents, which are problems needed be solved for all mankind, for the development of therapeutic agents utilizing the results of the research, and for the development of medical technologies and technologies for improving quality of life.

A virus is a small infectious agent (average of 0.1 um or less) that is smaller than bacteria and thereby cannot be filtered even with a bacterial filter (0.22 um), and is an organism that has only nucleic acid (DNA or RNA) and a small number of proteins as substances needed for survival, and thereby are dependent upon hosts. As therapeutic agents for diseases caused by viruses, drugs that weaken or kill the action of viruses infested into the body are referred to as antiviral therapeutic agents.

Immunotherapy a vaccines is currently a mainstream viral infectious disease treatment. Specifically, examples of therapeutic agent for the infectious disease caused by *chlamydia* (giant virus) such as trachoma and fourth venereal disease (venereal disease) comprise tetracycline and chloramphenicol, examples of a preventive agent for influenza A-type virus include amantadine, an idoxuridine (IDU) eye bath drop was developed as a preventive agent for herpes keratitis, and vidarabine/acyclovir have received attention as a simple herpes encephalitis (encephalitis) or an immunosuppressant. Particularly, interferon is a most promising drug for viral infectious diseases, and usefulness thereof is currently being examined.

Lately, the preference for natural substances in treating or preventing health issues has grown globally. This trend is affecting pharmaceutical companies, in that they are producing new antimicrobial agents extracted from plants. Accordingly, research on exploring new anti-viral materials from thousands of plant types has been constantly carried out globally, and various phytochemicals having antiviral activities, such as flavonoid, terpenoid, lignan, sulfide, polyphenols, coumarin, saponin, alkaloid, polyyne, thiophene, proteins and peptides have been identified. Several volatile essential oils of generally used edible herbs, spices and herb teas also have antiviral activities. However, with the exception of a few compound groups described above, most research on the active substances of medicinal plants having antiviral activities is in its beginning stages.

*Aleurites fordii* is a deciduous tree of Dicotyledone Geraniales Euphorbiaceae, its scientific name is *Aleurites fordii*, and it is often referred to as a Tung oil tree. China is the country of origin, and its fruits, leaves and roots have been used in traditional oriental medicines to treat sore throat, respiratory disease and constipation (Pencreach G. et al., *Anal. Biochem.*, 2002, 303, 17-24; Ito Y. et al., *Cancer Lett.*, 1983, 18, 87-95).

Numerous compounds such as diterpenoid ester, sterol, tannin, oil and coumarin have been obtained through the chemical component analysis of *Aleurites fordii* (Fozdar B. I. et al., *Phytochemistry*, 1989, 9, 2459-2461; Lee Y. C. et al., *J. Am. Pharmaceut. Assoc.*, 1959, 3, 162-165; Xie Y. F. et al., *Zhongguo Tianran Yaowu*, 2010, 8, 264-266). Among these, several biological activities such as piscicidal effects and Epstein-Barr virus activation have been reported for 12-O-hexadecanoyl-16-hydroxyphorbol-13-acetate (HHPA), a phorbol ester-based compound isolated from the leaf of *Aleurites fordii* (Hirota M. et al., *Agri. Bio. Chem.*, 1979, 43, 2523-2529). However, the application for the treatment of viral infectious diseases has not been reported.

DISCLOSURE

Technical Problem

In view of the above, the inventors of the present invention have made various efforts to identify natural product-derived materials having antiviral activities, and as a result, have isolated 4 known phorbol ester compounds in addition to 12-O-hexadecanoyl-7-oxo-5-ene-16-hydroxyphorbol-13-acetate, a novel phorbol ester compound, from the leaf of *Aleurites fordii*, then verified that the compounds enhance the production of interferon gamma (IFN-γ), an important cytokine in innate and acquired immunity against viruses and in bacterial infection between cells, in NK92 cells, and completed the present invention.

Technical Solution

A first object of the present invention is to provide a compound represented by Chemical Formula 1 or a pharmaceutically acceptable salt thereof.

A second object of the present invention is to provide a pharmaceutical composition for treating or preventing viral infectious diseases, which comprises a compound represented by Chemical Formulae 2 to 4 or a pharmaceutically acceptable salt thereof as an active ingredient.

A third object of the present invention is to provide a health functional food for preventing or ameliorating viral infectious diseases, which comprises a compound represented by Chemical Formulae 2 to 4 or a sitologically acceptable salt thereof as an active ingredient.

A fourth object of the present invention is to provide a composition for enhancing the production of interferon-gamma, which comprises a compound represented by Chemical Formulae 2 to 4 or a pharmaceutically acceptable salt thereof as an active ingredient.

A fifth object of the present invention is to provide a method for preventing or treating viral infectious diseases comprising administering a compound represented by Chemical Formulae 2 to 4 or a pharmaceutically acceptable salt thereof to a subject having a viral infectious disease occurrence or a risk thereof with a therapeutically effective dose.

Advantageous Effects

The present invention provides a phorbol-type novel diterpene compound isolated from the leaf of *Aleurites fordii*, and phorbol-type diterpene-based compounds derived from *Aleurites fordii* including the novel compound have activities of inducing the production of IFN-γ in NK cells, and thereby are effective in treating or preventing viral infectious diseases.

MODE FOR DISCLOSURE

In view of the above, the present invention provides a compound represented by the following Chemical Formula 1 or a pharmaceutically acceptable salt thereof.

[Chemical Formula 1]

In the present invention, the compound represented by Chemical Formula 1 is represented by Compound 1, and a name thereof is 12-O-hexadecanoyl-7-oxo-5-ene-16-hydroxyphorbol-13-acetate.

The Compound 1 is a phorbol-type diterpene compound, and is a novel material that the inventors of the present invention isolated from the leaf area of *Aleurites fordii*. The Compound 1 may have an activity facilitating or enhancing the interferon gamma production in cells.

In addition, the present invention provides a pharmaceutical composition for treating or preventing viral infectious diseases, which comprises a compound represented by the following Chemical Formulae 2 to 4 or a pharmaceutically acceptable salt thereof as an active ingredient.

[Chemical Formula 2]

-continued

[Chemical Formula 3]

[Chemical Formula 4]

In the formulae,
R₁ is CH₂OH or CH₃, and
R₂ is CH₃ or CH₂OH.

In the present invention, the phorbol-type diterpene compound represented by Chemical Formulae 2 to 4 may be isolated from *Aleurites fordii*, and preferably from the leaf area of *Aleurites fordii*.

In addition to the compound represented by Chemical Formulae 2 to 4 isolated from *Aleurites fordii*, the pharmaceutical composition of the present invention may comprise a chemically synthesized compound represented by Chemical Formulae 2 to 4 or a pharmaceutically acceptable salt thereof.

The present invention comprises not only the compound represented by Chemical Formulae 2 to 4 and the pharmaceutically acceptable salt thereof, but also all solvates, hydrates or racemates that can be prepared therefrom.

The term "prevention" in the present invention means all actions that suppress viral infectious diseases or delay the outbreak of diseases by the administration of the composition.

The term "treatment" in the present invention means all actions that enable symptoms by virus infection ameliorate or change for the better by the administration of the composition.

In the present invention, the viral infectious disease may be a disease caused by one or more viruses selected from the group consisting of influenza virus, Influenza A virus subtype H1N1, avian influenza virus, rhinovirus, adenovirus, coronavirus, parainfluenza virus, respiratory syncytial virus, Herpesvirus (HSV), human immunodeficiency virus (HIV), rotavirus and hepatitis virus, but the virus is not limited thereto.

In addition, the viral infectious disease may be one or more viral infectious diseases selected from the group consisting of a rotaviral infectious disease, an adenoviral infectious disease, influenza, cold, a sore throat, bronchitis, pneumonia, avian influenza, eye inflammation, encephalitis, acquired immunodeficiency syndrome, hepatitis and severe acute respiratory syndrome (SARS), but the viral infectious disease is not limited thereto. Such viruses may be treated by interferon-γ, and one embodiment of the present invention verified that the compounds enhance the production of interferon-γ, therefore, it was verified that the compounds are effective in treating virus infection.

The compound represented by Chemical Formulae 2 to 4 of the present invention may have a form of a pharmaceutically acceptable salt, and as the salt, an acid addition salt formed by a pharmaceutically acceptable free acid may be used. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono- and dicarboxylate, phenyl-substituted alkanoate, hydroxyalkanoate and alkanedioate, aromatic acids, aliphatic and aromatic sulfonic acids. Such pharmaceutically nontoxic salts comprise sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butene-1,4-dioate, hexane-1,6-dioate, benzoate, chlorobenzoate, methyl benzoate, dinitrobenzoate, hydroxybenzoate, methoxybenzoate, phthalate, terephthalate, benzenesulfonate, toluenesulfonate, chlorobenzenesulfonate, xylenesulfonate, phenyl acetate, phenyl propionate, phenyl butyrate, citrate, lactate, β-hydroxybutyrate, glycolate, malate, tartrate, methanesulfonate, propanesulfonate, naphthalene-1-sulfonate, naphthalene-2-sulfonate or mandelate.

The acid addition salt according to the present invention may be prepared by common methods such as dissolving the compound of Chemical Formula 2, 3 or 4 in an excess aqueous acid solution, and precipitating this salt using a water-miscible organic solvent such as methanol, ethanol, acetone or acetonitrile.

In addition, a pharmaceutically acceptable metal salt may be prepared using a base. An alkali metal or alkaline-earth metal salt is obtained by, for example, dissolving the compound in an excess alkali metal hydroxide or alkaline-earth metal hydroxide solution, filtering the non-soluble compound salt, drying the filtrate and drying the result. Herein, preparing a sodium, potassium or calcium salt as the metal salt is pharmaceutically suitable. Furthermore, a silver salt corresponding to this is obtained by reacting the alkali metal or alkaline-earth metal salt with a suitable silver salt (for example, silver nitrate).

The composition of the present invention may comprise a pharmaceutically acceptable carrier. The composition including a pharmaceutically acceptable carrier may have various oral or non-oral formulations. When formulated, the composition is prepared using a filler, an extending agent, a bonding agent, a wetting agent, a disintegrating agent, a diluent such as a surfactant or a diluting agent commonly used. Solid formulations for oral administration comprise tablets, pills, powders, granules, capsules and the like, and these solid formulations are prepared by mixing one or more compounds with at least one or more diluting agents such as starch, potassium carbonate, sucrose or lactose and gelatine. In addition, lubricants such as magnesium stearate and talc are also used in addition to simple diluting agents. Liquid formulations for oral administration comprise suspensions, oral solutions, emulsions, syrups and the like, and various diluting agents such as a wetting agent, a sweeting agent, a flavoring agent and a preserving agent may be comprised therein in addition to commonly used diluents such as water and liquid paraffin. The formulations for non-oral administration comprise sterilized aqueous solutions, non-aqueous solvents, suspensions, emulsions, freeze-dried formulations and suppositories. The non-aqueous solvent and the suspension may be comprised of propylene glycol, polyethylene glycol, vegetable oil such as olive oil, and injectable ester such as ethylolate. As the base of suppository, witepsol, macrogol, tween 61, cacao butter, laurin butter, glycerogelatin and the like may be used.

Meanwhile, the present invention provides a method for preventing or treating viral infectious diseases including administering the composition of the present invention to a subject having a viral infectious disease occurrence or a risk thereof with a therapeutically effective dose.

The term "subject" in the present invention means all animals including human beings already infected or having a possibility to be infected by viruses, and the diseases can be effectively prevented and treated by administering the composition of the present invention to the subject.

The composition of the present invention may be administered in combination with existing therapeutic agents for viral infectious diseases. The composition may be administered through any general path as long as the composition reaches a target tissue. The composition of the present invention may be administered by intraperitoneal administration, intravenous administration, intramuscular administration, subcutaneous administration, intracutaneous administration, oral administration, intranasal administration, pulmonary administration or rectal administration depending on the purpose, but the administration method is not limited thereto. In addition, the composition may be administered by any apparatus capable of moving an active material to a target cell.

The composition of the present invention is administered with a therapeutically effective dose. The term "therapeutically effective dose" means an amount sufficient to treat diseases in a reasonable benefit/risk ratio applicable to medical treatments, and the level of the effective dose may be determined depending on factors including the types of subjects, severity, age, gender, the types of infecting viruses, the activity of drugs, the sensitivity to drugs, administration time, administration paths and excretion rates, treatment period and drugs simultaneously used, and other factors well-known in the field of medicine. The composition of the present invention may be administered as an individual therapeutic agent or as a combination with other therapeutic agents, and the composition of the present invention may be administered consecutively or simultaneously with existing therapeutic agents. In addition, the composition of the present invention may be administered by single or multiple administration. It is important to administer the amount capable of obtaining a maximum effect with a minimal amount without side effects considering all the factors described above, and the amount may be readily determined by those skilled in the art.

The composition of the present invention may be used for preventing and treating virus infection either alone, or as a combination with methods such as surgery, hormone treatments, medication treatments and methods using biologic response modifiers.

In the examples of the present invention, the compound represented by the following Chemical Formula 2, the compound represented by the following Chemical Formula 3 and the compound represented by the following Chemical Formula 4 are isolated from *Aleurites fordii*, and identified.

[Chemical Formula 2]

[Chemical Formula 3]

[Chemical Formula 4]

In the formulae, $R_1$ is $CH_2OH$ or $CH_3$, and $R_2$ is $CH_3$ or $CH_2OH$.

In the present invention, the compound represented by Chemical Formula 2 in which $R_1$ is $CH_2OH$ is represented by Compound 1, the compound represented by Chemical Formula 2 in which $R_1$ is $CH_3$ is represented by Compound 2, the compound represented by Chemical Formula 3 in which $R_2$ is $CH_3$ is represented by Compound 3, the compound represented by Chemical Formula 3 in which $R_2$ is $CH_2OH$ is represented by Compound 4, and the compound represented by Chemical Formula 4 is represented by Compound 5.

The name of Compound 1 is 12-O-hexadecanoyl-7-oxo-5-ene-16-hydroxyphorbol-13-acetate, the name of Compound 2 is 12-O-hexadecanoyl-7-oxo-5-ene-phorbol-13-acetate, the name of Compound 3 is 12-O-hexadecanoyl-phorbol-13-acetate, the name of Compound 4 is 12-O-hexadecanoyl-16-hydroxyphorbol-13-acetate, and the name of Compound 5 is 12-O-hexadecanoyl-4-deoxy-4α-16-hydroxyphorbol-13-acetate.

Figure 7:
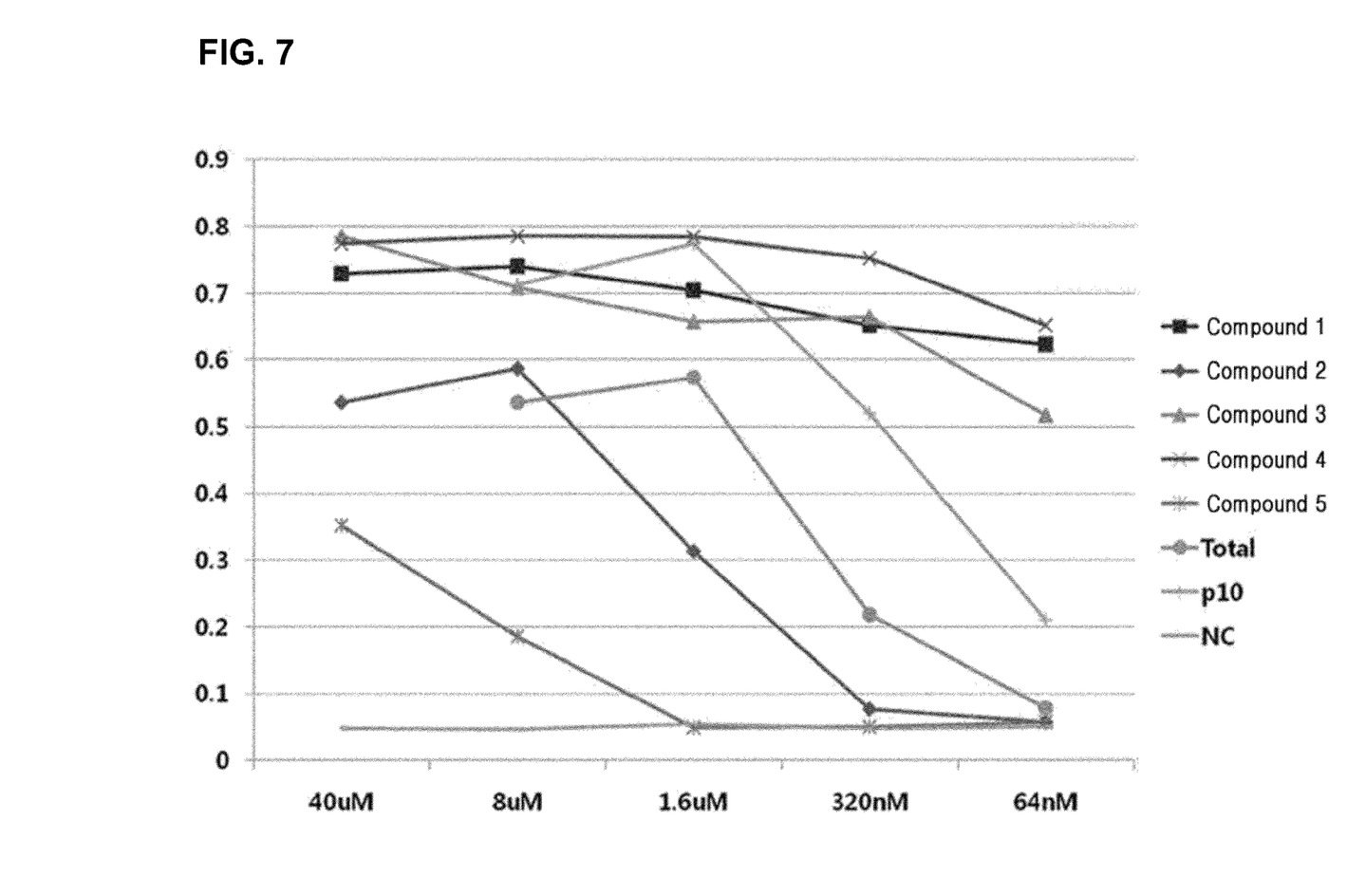
FIG. 7 and FIG. 8 are graphs showing the effects of Compounds 1 to 5 each with a different concentration on the production of IFN-γ in human natural killer cells (NK92). Herein, with each of the compounds of the present invention, an *Aleurites fordii* methanol extract (Total), a *Daphne genkwa* methanol extract (P10), genkwadaphnin (GD), yuanhuacine (YH) and phorbol 12-myristate 13-acetate (PMA) are used as a positive control group. Each value is an average±standard deviation value obtained by culture carried out three times.
Figure 8:
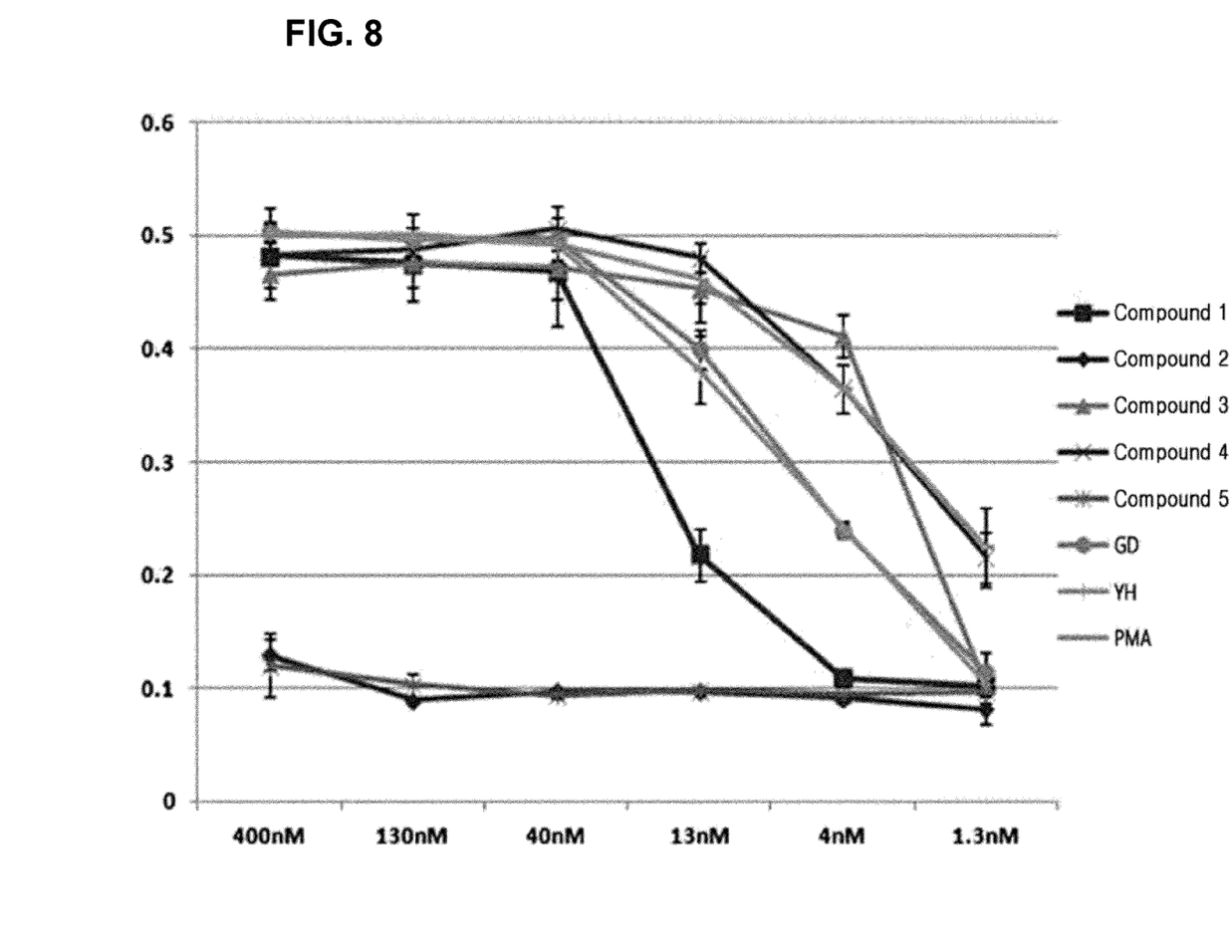

In the examples of the present invention, the effects of the compounds (1 to 5) on the expression of IFN-γ in NK92 cells are investigated using an ELISA analysis, and it is verified that the compounds 1 to 5 induce the production of IFN-γ in NK92 cells (FIG. 7 and FIG. 8). These results show that the compounds 1 to 5 identified in the present invention may be used as useful antiviral agents by facilitating or enhancing the production of IFN-γ in cells.

Furthermore, the present invention provides a health functional food for preventing or ameliorating viral infectious diseases, which comprises the compound represented by Chemical Formulae 2 to 4 or a sitologically acceptable salt thereof as an active ingredient. In other words, the compound represented by Chemical Formulae 2 to 4 or the sitologically acceptable salt thereof may be added to foods with the purpose of preventing or ameliorating viral infectious diseases.

In the present invention, "prevention" means all actions that suppress viral infectious diseases or delay the outbreak of diseases by the intake of the health functional foods, and "treatment" means all actions that enable symptoms by virus infection ameliorate or change for the better by the intake of the health functional foods.

The health functional food of the present invention comprises all forms such as functional health foods, nutritional supplements, nutritionals, pharmafoods, health foods, nutraceuticals, designer foods, food additives and feed additives.

When the compound of Chemical Formulae 2 to 4, or the sitologically acceptable salt thereof is added as an additive of a health functional food, the compound or the sitologically acceptable salt thereof may be added either alone or together with other foods or food ingredients, and may be suitably used according to common methods. The amount of mixed active ingredients may be properly determined depending on the purpose of use (use for prevention or amelioration).

The types of the foods are not particularly limited, and examples thereof comprise meat, sausage, bread, chocolate, candies, snacks, cookies, pizza, ramen, other noodles, gums, dairy products including ice cream, various soups, beverages, teas, health drinks, alcoholic beverages and vitamin complexes and the like, and comprise all health functional foods in an acceptable meaning.

In addition to the above, the health functional food of the present invention may contain various nutritionals, vitamins, electrolytes, flavoring agents, coloring agents, pectic acid and a salt thereof, alginic acid and a salt thereof, organic acids, protective colloidal viscosity agents, pH regulating agents, stabilizing agents, preservatives, glycerin, alcohols, carbonating agents used in carbonated beverages, and the like.

Furthermore, in addition to these, the health functional food of the present invention may contain flesh for preparing natural fruit juices, fruit juice beverages and vegetable beverages.

The viral infectious diseases are the same as described above.

In addition, the present invention provides a composition for enhancing the production of interferon-gamma, which comprises the compound represented by Chemical Formulae 2 to 4 or the pharmaceutically acceptable salt thereof as an active ingredient.

The composition for enhancing the production of interferon-gamma may further comprise a pharmaceutically acceptable carrier, and the pharmaceutically acceptable carrier is the same as described above.

In the examples of the present invention, when the compound represented by Chemical Formulae 2 to 4 is applied to NK92 cells, it is verified that the IFN-γ expression in the NK92 cells increased (FIG. 7 and FIG. 8). Therefore, the compound represented by Chemical Formulae 2 to 4 or the pharmaceutically acceptable salt thereof enhances the IFN-γ production in cells, preferably in NK cells, and thereby is ultimately useful in preventing or treating viral infectious diseases.

Hereinafter, the constitutions and the effects of the present invention will be described in more detail with reference to examples, however, these examples are for illustrative purposes only, and the scope of the present invention is not limited thereto.

Example 1

Materials and Methods

General Experimental Procedure

The optical rotation was measured using a Jasco P2000 polarimeter (Jasco Corporation, Japan). The UV data were obtained on a UV-VIS spectrometer 2400 (Shimadzu Co. Ltd., Japan), and the NMR spectra were recorded on a Varian UNITY 400 (Varian, Inc., Palo Alto, Calif.) using tetramethylsilane as an internal standard material. The HRESIMS was carried out on a Waters Q-Tof Premier spectrometer (Micromass UK Ltd., Manchester, UK). The column chromatography was carried out using silica gel (230-400 mesh, SiliCycle Inc., Quebec, Canada), RP-C18 (Cosmosil 75C18-PREP, Kyoto, Japan), and Sephadex LH-20 (25-100 μm, Sigma-Aldrich, Steinheim, Germany). The TLC was carried out on a precoated Kiesel-gel 60 F254 (0.25 mm, Merck, Darmstadt, Germany) and Kiesel-gel 60 RP-18F254s (0.25 mm, Merck, Steinheim, Germany).

Plant Material

Leaves of *Aleurites fordii* used were collected in Seogwipo, Jejudo.

Cell Culture

NK92 cells (human NK lymphoma) were obtained from American Type Culture Collection. NK92 cells were kept in α-MEM (Invitrogen, US) containing 20% fetal bovine serum (Invitrogen), 2 mM L-glutamate, 100 mg/mL penicillin and 100 mg/mL streptomycin (Invitrogen), and were replenished with 100 U/mL IL-2 (Peprotech, US). NK92 cell culture was carried out in a culture medium at 37° C. under 5% $CO_2$ humidity atmosphere. The amount of human IFN-γ was analyzed according to the protocol of a supplier using an assay kit (Endogen, Woburn, US).

Example 2

Extraction and Isolation 2.9 kg of the *Aleurites fordii* leaf dried in the atmosphere was grinded, and extracted 3 times with MeOH at room temperature to give 449.6 g of a solid extract. The MeOH extract was suspended in $H_2O$, and then partitioned to n-hexane, EtOAc, and n-BuOH continuously to give 96.3 g, 53.9 g and 85.9 g of residues, respectively. The hexane extract showed higher IFN-γ inducing activity compared to other solvent extracts. Accordingly, the hexane extract was column chromatographed (CC) on silica gel (230 to 400 mesh) using hexane/EtOAc (50:1 to 1:5) as an eluent, and then silica gel column chromatographed once again using $CHCl_3$/MeOH (10:1 to 1:1) to give 38 fractions (LH1 to LH38). Active fractions LH30 and LH31 were mixed together since they were shown to be similar on a TLC chromatogram, and then the result was chromatographed on a RP-C18 (75$C_{18}$-PREP) medium pressure liquid chromatography (MPLC) column using a stepwise concentration gradient mixture of MeOH—$H_2O$ (45:55 to 90:10) as an eluent to give 21 subfractions (LH3031-1 to LH3031-21). Fraction LH3031-20 (30 mg) was once again silica gel column chromatographed using hexane/EtOAc (2.5:1) to give Compound 2 (2.6 mg) and Compound 3 (13 mg). Fraction LH3435, a combination of active fractions LH34 and LH35, was silica gel column chromatographed using $CHCl_3$/MeOH (50:1, 20:1) to give subfractions LH3435-1 to LH3435-11. Fraction LH3435-7 (1.2 g) was once again fractioned with Sephadex LH20 column chromatography using hexane/$CH_2Cl_2$/MeOH (10:10:1) as an eluent to give subfractions LH3435-7-1 to LH3435-7-8. Next, LH3435-7-2 (784 mg) was once again chromatographed on a silica gel column chromatography using a concentration gradient solvent of $CHCl_3$/acetone (5:1, 4:1) to give Compound 1 (39.8 mg) and Compound 4 (278 mg). Fraction N3435-3 (50.1 mg) was Sephadex LH20 column chromatographed using hexane/$CH_2Cl_2$/MeOH (10:10:1) as an eluent to give 4 subfractions LH3435-3-1 to LH3435-3-4. Next, LH3435-3-2 (30 mg) was preparative layer chromatographed (PLC) using $CHCl_3$/acetone (2:1) to give LH-3-2-P, and LH-3-2-P was further purified through preparative HPLC (C18, 5 μm, 92% ACN) to give Compound 5 (6.0 mg).

Example 3

Compound Identification

Figure 1:
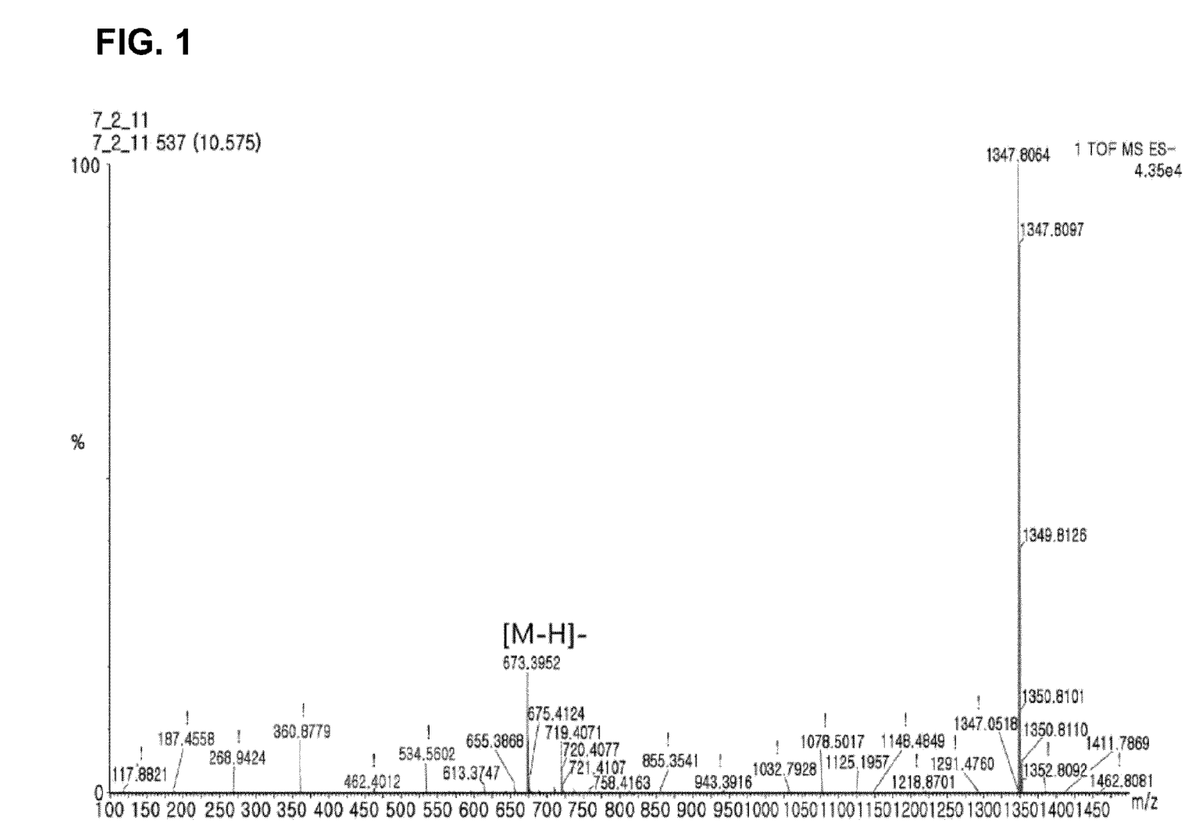
FIG. 1 shows a High Resolution Electron Spray Ionization Mass Spectrum (HRESIMS) of Compound 1.
Figure 2:
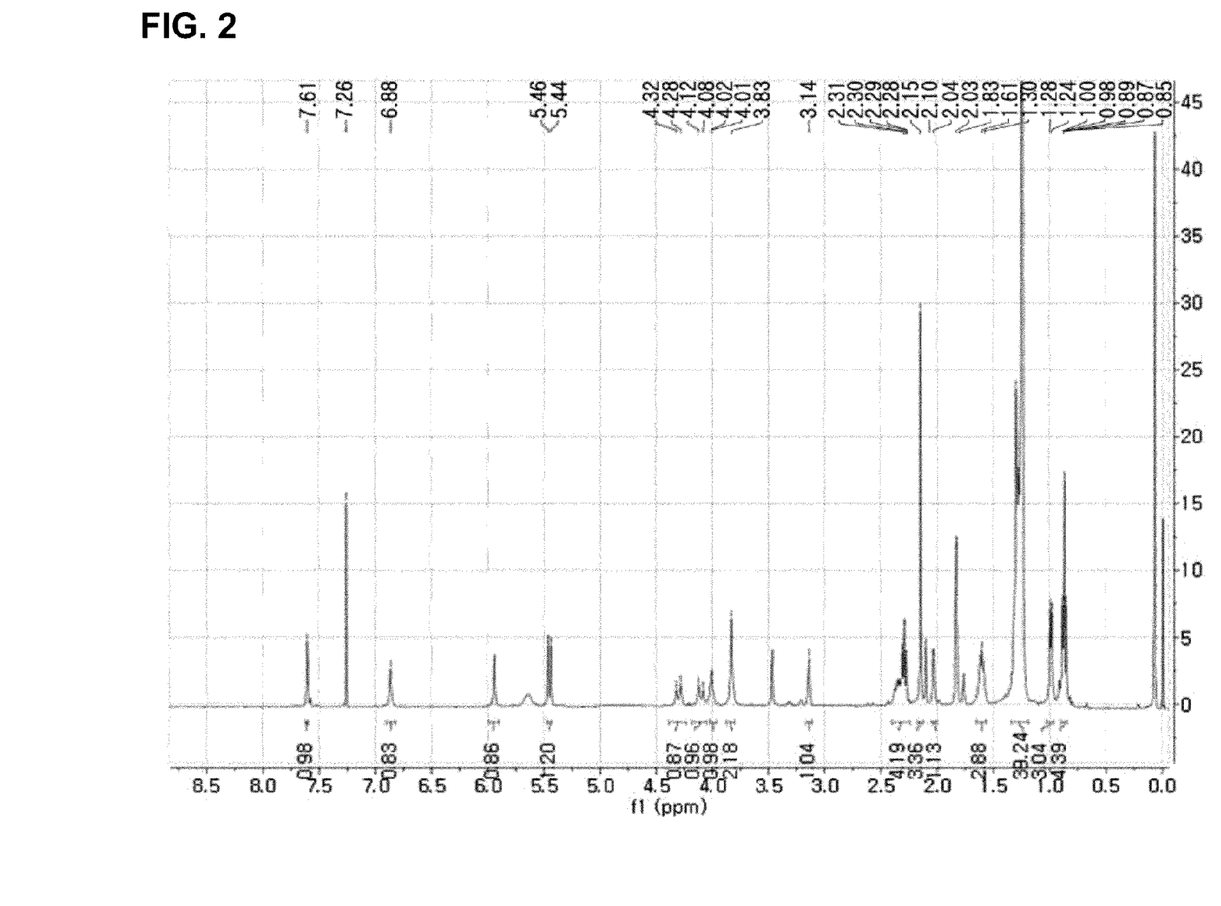
FIG. 2 shows a $^1$H spectrum of Compound 1.
Figure 3:
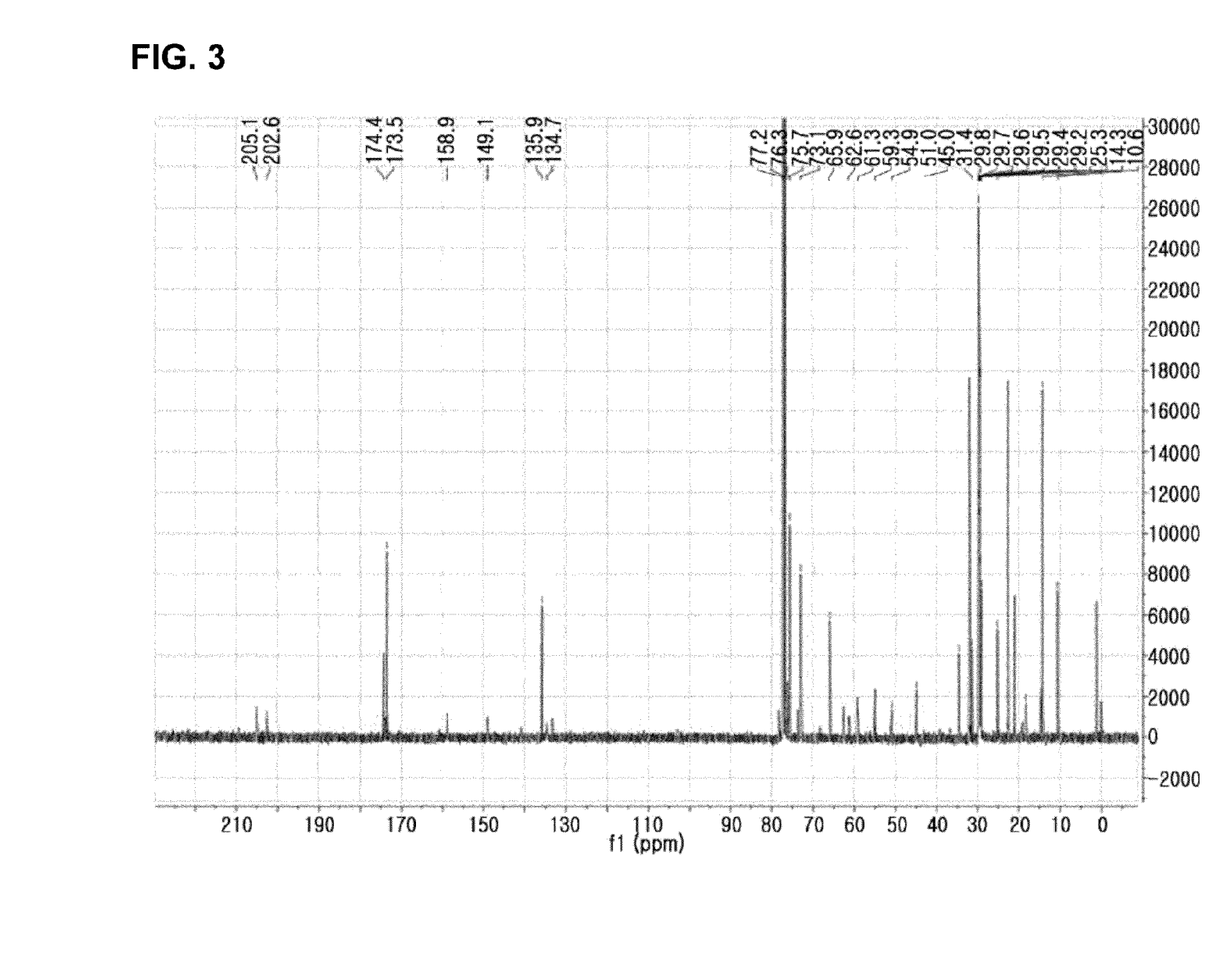
FIG. 3 shows a $^{13}$C spectrum of Compound 1.
Figure 4:
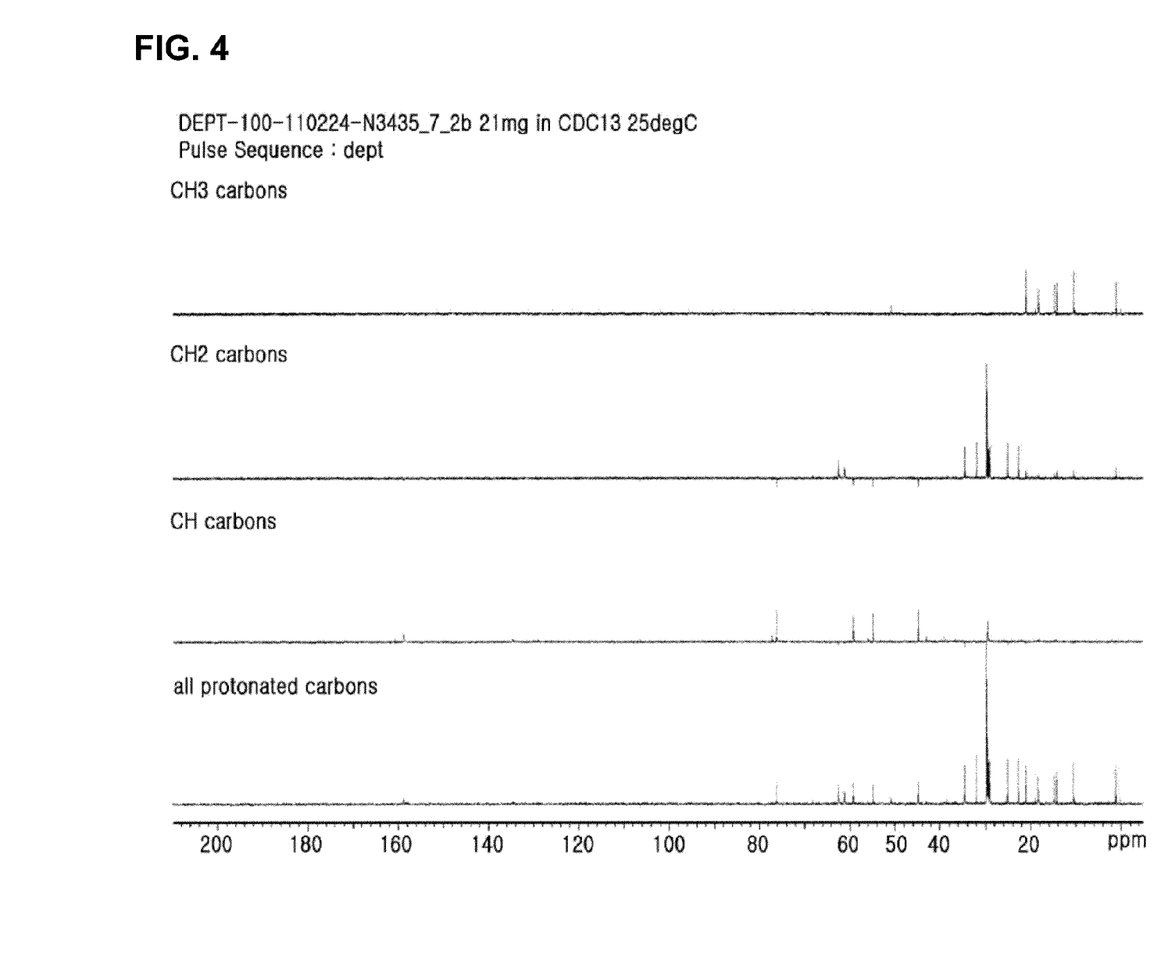
FIG. 4 shows a DEPT spectrum of Compound 1.
Figure 5:
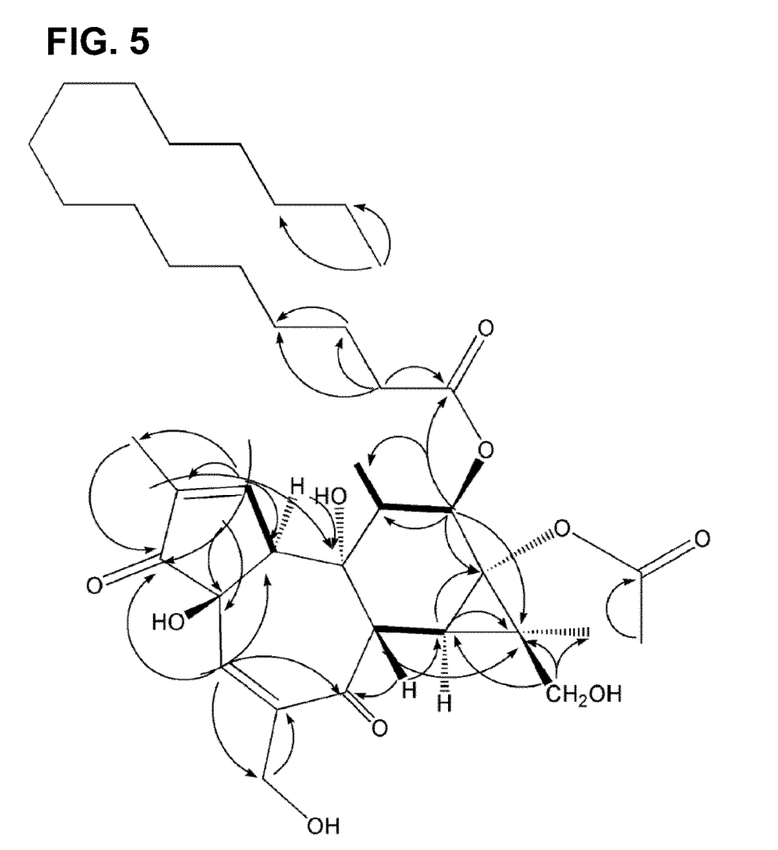
FIG. 5 shows HMBC (H→C) correlation and COSY (H—H) correlation of Compound 1.

Compound 1 was isolated as white noncrystalline solids. The molecular formula thereof was identified as $C_{38}H_{58}O_{10}$ through the [M-H]⁻ molecular ion peak of 673.3953 shown in a High Resolution Electron Spray Ionization Mass Spectrum (HRESIMS) (FIG. 1). The $^1H$, $^{13}C$ and DEPT spectra of Compound 1 exhibited 2 double bonds, 4 carbonyl groups, 5 methyl groups, 2 oxygenated methylene groups, 5 methine groups and 4 quaternary carbons (3 oxygenated) (FIG. 2 to FIG. 4). It was seen from the large wide peak at $δ_H$ 1.24 of $^1H$ spectrum that a long chain unit of carbon exists within this compound. In the HMBC spectrum, one olefin proton $δ_H$ at 6.86 (H-5) showed correlation with oxygenated carbon at $δ_C$ 61.3 (C-20) and 2 carbonyl groups at $δ_C$ 205.1 (C-3) and 202.6 (C-7), and another olefin proton $δ_H$ at 7.61 (H-1) showed resonance with a methyl group at 10.6 (C-19) and a carbonyl group at 205.1 (C-3). This shows the presence of 2 α,β-unsaturated ketone skeletons within this compound, and shows that these skeletons are not far from each other. In addition, signals exist between $δ_H$ 3.83 (H-16) and $δ_C$ 18.4 (C-17), however, 2 singlet protons each showed correlation with C-14 in which the proton is shown as doublet, and C-15 (quaternary carbon). This shows that these carbons form a gem-disubstituted-cyclopropane portion. In addition, 2 carbonyl groups were exhibited at $δ_C$ 173.5 and 174.4. The first peak showed correlation with the protons at $δ_H$ 5.45 (H-12), $δ_H$ 2.30 and 1.60, however, the second peak showed a possibility of being in contact with singlet methyl at $δ_H$ 2.15 (H-22). Based on the data above, it was seen that the carbon at $δ_C$ 174.4 belonged to the acetate group, and the other carbon was a component of the 16-carbon ester chain identified in mass spectroscopy. The HMBC (H→C) correlation and the COSY (H—H) correlation of Compound 1 were shown in FIG. 5.

Based on the data above, the carbon skeleton of Compound 1 was surmised to be partially similar to 12-O-decanoylphorbol-13-acetate (Patricia Y. H. et al., *J. Nat. Prod.*, 2010, 73, 1907-1913) derived from Pimelea elongate and identified as a phorbol-type diterpene. All the $^1H$ and $^{13}C$-NMR signals of Compound 1 were similar except that hydroxymethylene (C-16) were present in Compound 1 instead of a methyl signal in Compound 2. Based on the information above, the structure of Compound 1 was identified as 12-O-hexadecanoyl-7-oxo-5-ene-16-hydroxyphorbol-13-acetate.

Compound 2 was obtained as colorless oil and showed a molecular ion [M-H]⁻ of m/z 657.3969 in a HRESIMS corresponding to a molecular formula $C_{38}H_{58}O_9$. When compared with Compound 1, the $^1H$ and $^{13}C$ NMR data of Compound 2 were identical to those of Compound 1 except that the methyl group was substituted with hydroxymethylene at C-16. Therefore, the structure of Compound 2 was identified as 12-O-hexadecanoyl-7-oxo-5-ene-phorbol-13-acetate. This compound has been reported previously as a compound isolated from a Chinese tallow tree (*Sapium sebiferum*) (Ohigashi H. et al., *Agri. Bio. Chem.*, 1983, 7, 1617-1622), however, the properties of this compound have not been reported.

Compound 3 was obtained as colorless oil and showed a molecular ion peak [M-H]⁻ of m/z 643.4244 in a HRESIMS corresponding to a molecular formula of $C_{38}H_{60}O_8$. The $^1H$ and $^{13}C$-NMR signals of Compound 3 were identical to literature NMR data of 12-O-decanoylphorbol-13-acetate except for the differences in the 16-carbon ester chain identified with mass spectroscopy. Therefore, Compound 3 was identified as 12-O-hexadecanoyl-phorbol-13-acetate.

Compound 4 was isolated as white noncrystalline powders and showed a molecular ion peak [M-H]⁻ of m/z 659.4143 in a HRESIMS corresponding to a molecular formula of $C_{38}H_{60}O_9$. The $^1H$ and $^1C$ NMR spectra of Compound 4 comprise practically the same signals with the spectra of Compound 3 except that the methyl group was substituted with hydroxymethylene at C-16. Therefore, the structure of Compound 4 was identified as 12-O-hexadecanoyl-16-hydroxyphorbol-13-acetate.

Figure 6:
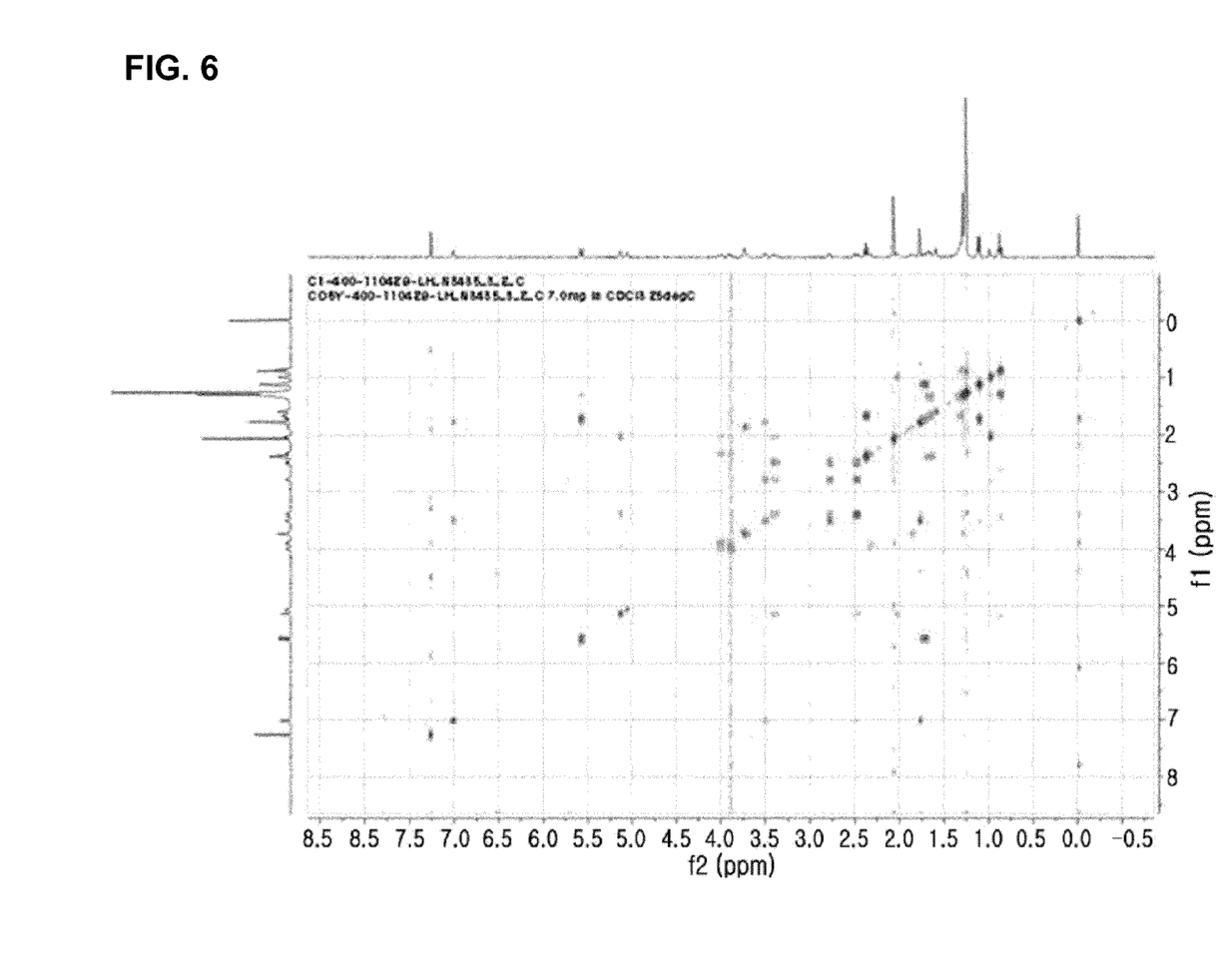
FIG. 6 shows a $^1$H—$^1$H COSY spectrum of Compound 5.

Compound 5 was obtained as colorless oil and showed a molecular ion peak [M+FA-H]⁻ of m/z 689.4296 in a HRESIMS corresponding to a molecular formula of $C_{38}H_{60}O_8$. The signals within the $^1H$ and $^1C$ NMR spectra of Compound 5 were identical to the signals of Compound 4 except that the oxygenated quaternary carbon at $\delta_C$ 73.1 (C-4) was reduced to tertiary carbon at $\delta_C$ 49.5. In the $^1H$—$^1H$ COSY spectrum (FIG. 6), the proton at $\delta_H$ 2.78 (H-4) showed correlation with the proton at $\delta_H$ 3.51 (H-10), and there was a cross-peak between C-4, and H1 and H5. Therefore, the structure of Compound 5 was identified as 12-O-hexadecanoyl-4-deoxy-4α-16-hydroxyphorbol-13-acetate.

Physicochemical properties and spectroscopic data of Compounds 1 to 5 are shown below:

12-O-hexadecanoyl-7-oxo-5-ene-16-hydroxyphorbol-13-acetate (1)

white noncrystalline solids; $[\alpha]^{20}_D$+10.7° (c 1.68, $CHCl_3$); UV (EtOH); λmax (log ε) 222 (2.84) nm; $^1H$ and $^{13}C$ NMR data, refer to the following Tables 1 and 2; HRESIMS m/z 673.3953 [M-H]⁻ (calculated for $C_{38}H_{57}O_{10}$, 673.3952).

12-O-hexadecanoyl-7-oxo-5-ene-phorbol-13-acetate (2)

colorless oil; $[\alpha]^{20}_D$+41.5° (c 0.11, $CHCl_3$); UV (EtOH); λmax (log ε) 221 (2.46) nm; $^1H$ and $^{13}C$ NMR data, refer to the following Tables 1 and 2; HRESIMS m/z 657.3969 [M-H]⁻ (calculated for $C_{38}H_{57}O_9$, 657.4003).

12-O-hexadecanoyl-phorbol-13-acetate (3)

colorless oil; $[\alpha]^{20}_D$+42.6° (c 0.21, $CHCl_3$); UV (EtOH); λmax (log ε) 202 (3.22), 228 (1.80) nm; $^1H$ and $^{13}C$ NMR data, refer to the following Tables 1 and 2; HRESIMS m/z 643.4244 [M-H]⁻ (calculated for $C_{38}H_{59}O_8$, 643.4210).

12-O-hexadecanoyl-16-hydroxyphorbol-13-acetate (4)

noncrystalline white powders; $[\alpha]^{20}_D$+61.06° (c 0.34, $CHCl_3$); UV (EtOH); λmax (log ε) 203 (3.32), 227 (1.92) nm; $^1H$ and $^{13}C$ NMR data, refer to the following Tables 1 and 2; HRESIMS m/z 659.4143 [M-H]⁻ (calculated for $C_{38}H_{59}O_9$, 659.4159).

12-O-hexadecanoyl-4-deoxy-4α-16-hydroxyphorbol-13-acetate (5)

colorless oil; $[\alpha]^{20}_D$ b (c 0.45, $CHCl_3$); UV (EtOH); λmax (log ε) 232 (2.62) nm; $^1H$ and $^{13}C$ NMR data, refer to the following Tables 1 and 2; HRESIMS m/z 689.4296 [M-H]⁻ (calculated for $C_{39}H_{61}O_{10}$, 689.4265).

TABLE 1

| H | 1 | 2 | 3 | 4 | 5 |
|---|---|---|---|---|---|
| 1 | 7.61 brs | 7.66 brs | 7.58 brs | 7.56 brs | 7.01 brs |
| 2 | | | | | |
| 3 | | | | | |
| 4 | | | | | 2.78 m |
| 5 | 6.86 s | 6.90 brs | 2.56 d (19.2) | 2.61 d (19.2) | 3.40 dd (15.6, 2.5) |
|   |        |          | 2.48 d (19.2) | 2.40 d (19.2) | 2.48 dd (15.6, 5.0) |
| 6 | | | | | |
| 7 | | | 5.67 d (5.1) | 5.66 d (4.5) | 5.14 brs |
| 8 | 4.01 d (4.2) | 3.73 d (5.3) | 3.25 brs | 3.35 brs | 2.03 brs |
| 9 | | | | | |
| 10 | 3.14 brs | 3.31 m | 3.25 brs | 3.21 brs | 3.51 m |
| 11 | 2.36 m | 2.20 m | 2.14 m | 2.21 m | 1.73 m |
| 12 | 5.45 d (10.1) | 5.45 d (10.4) | 5.40 d (10.3) | 5.43 d (10.2) | 5.58 d (10.4) |
| 13 | | | | | |
| 14 | 2.03 d (5.3) | 1.85 | 1.08 d (5.2) | 1.24 | 0.98 d (5.1) |
| 15 | | | | | |
| 16 | 3.83 s | 1.20 | 1.24 s | 3.81 s | 3.73 s |
| 17 | 1.29 s | 1.19 | 1.21 s | 1.32 s | 1.29 s |
| 18 | 0.99 d (6.1) | 0.94 d (6.4) | 0.88 | 0.90 d (6.4) | 1.11 d (6.3) |
| 19 | 1.83 d (1.5) | 1.84 | 1.77 dd (2.8, 1.1) | 1.75 d (1.8) | 1.77 brs |

TABLE 1-continued

| H | 1 | 2 | 3 | 4 | 5 |
|---|---|---|---|---|---|
| 20 | 4.31 d (15.8) | 4.39 d (14.2) | 4.04 d (13.0) | 4.01 d (13.0) | 4.01 (11.3) |
| 21 | 4.10 d (15.8) | 4.29 d (14.2) | 3.98 d (13.0) | 3.97 d (12.9) | 3.89 (12.4) |
| 22 | 2.15 s | 2.11 s | 2.09 s | 2.10 s | 2.07 s |
| 1' | | | | | |
| 2' | 2.30 m | 2.32 m | 2.32 m | 2.30 m | 2.37 m |
| 3' | 1.60 m | 1.64 m | 1.63 m | 1.61 m | 1.67 m |
| 4' | 1.24 | 1.25 | 1.25 | 1.24 | 1.26 |
| 5' | 1.24 | 1.25 | 1.25 | 1.24 | 1.26 |
| 6' | 1.24 | 1.25 | 1.25 | 1.24 | 1.26 |
| 7' | 1.24 | 1.25 | 1.25 | 1.24 | 1.26 |
| 8' | 1.24 | 1.25 | 1.25 | 1.24 | 1.26 |
| 9' | 1.24 | 1,25 | 1.25 | 1.24 | 1.26 |
| 10' | 1.24 | 1.25 | 1.25 | 1.24 | 1.26 |
| 11' | 1.24 | 1.25 | 1,25 | 1.24 | 1.26 |
| 12' | 1.24 | 1.25 | 1,25 | 1.24 | 1.26 |
| 13' | 1.24 | 1.25 | 1.25 | 1.24 | 1.26 |
| 14' | 1.24 | 1.26 | 1.25 | 1.24 | 1.26 |
| 15' | 1.27 | 1.27 | 1.27 | 1.27 | 1.27 |
| 16' | 0.87 t (7.0) | 0.87 t (7.0) | 0.87 t (7.1) | 0.87 t (7.0) | 0.88 t (7.0) |

TABLE 2

| H | 1 | 2 | 3 | 4 | 5 |
|---|---|---|---|---|---|
| 1 | 158.9 | 159.8 | 160.9 | 160.7 | 155.6 |
| 2 | 135.9 | 135.2 | 133.0 | 133.2 | 143.8 |
| 3 | 205.1 | 204.9 | 209.0 | 209.5 | 212.9 |
| 4 | 73.1 | 73.2 | 73.8 | 73.6 | 49.5 |
| 5 | 134.7 | 137.4 | 38.7 | 38.4 | 25.3 |
| 6 | 149.1 | 148.5 | 140.6 | 140.9 | 137.7 |
| 7 | 202.6 | 201.5 | 129.3 | 128.9 | 125.9 |
| 8 | 54.9 | 54.9 | 39.2 | 39.1 | 40.7 |
| 9 | 75.7 | 75.6 | 78.4 | 78.3 | 78.2 |
| 10 | 59.3 | 59.2 | 56.3 | 56.0 | 47.4 |
| 11 | 45.0 | 44.5 | 43.0 | 43.1 | 43.5 |
| 12 | 76.3 | 76.1 | 76.7 | 76.4 | 75.5 |
| 13 | 65.9 | 65.7 | 65.8 | 66.0 | 65.5 |
| 14 | 29.6 | 29.4 | 36.4 | 36.6 | 37.9 |
| 15 | 31.4 | 25.3 | 25.8 | 31.8 | 31.4 |
| 16 | 62.5 | 16.8 | 16.9 | 62.3 | 62.6 |
| 17 | 18.4 | 23.6 | 24.0 | 18.9 | 19.8 |
| 18 | 14.8 | 14.6 | 14.6 | 14.6 | 12.1 |
| 19 | 10.6 | 10.4 | 10.2 | 10.1 | 10.6 |
| 20 | 61.3 | 63.7 | 68.0 | 68.2 | 69.3 |
| 21 | 174.4 | 173.8 | 173.9 | 173.8 | 173.4 |
| 22 | 21.1 | 21.1 | 21.2 | 21.1 | 21.1 |
| 1' | 173.5 | 173.7 | 173.9 | 173.4 | 172.9 |
| 2' | 34.7 | 34.5 | 34.7 | 34.6 | 34.7 |
| 3' | 25.3 | 25.2 | 25.3 | 25.2 | 25.2 |
| 4' | 29.2 | 29.1 | 29.2 | 29.1 | 29.2 |
| 5' | 29.4 | 29.4 | 29.4 | 29.3 | 29.4 |
| 6' | 29.5 | 29.5 | 29.5 | 29.4 | 29.5 |
| 7' | 29.5 | 29.6 | 29.7 | 29.4 | 29.6 |
| 8' | 29.7 | 29.7 | 29.7 | 29.6 | 29.7 |
| 9' | 29.8 | 29.7 | 29.8 | 29.7 | 29.8 |
| 10' | 29.8 | 29.7 | 29.8 | 29.7 | 29.8 |
| 11' | 29.8 | 29.8 | 29.8 | 29.7 | 29.8 |
| 12' | 29.8 | 29.8 | 29.8 | 29.8 | 29.8 |
| 13' | 29.8 | 29.8 | 29.8 | 29.8 | 29.8 |
| 14' | 31.9 | 32.0 | 32.1 | 31.8 | 31.9 |
| 15' | 22.7 | 22.8 | 22.8 | 22.8 | 22.7 |
| 16' | 14.3 | 14.2 | 14.3 | 14.2 | 14.1 |

Example 4

Investigation on IFN-γ Production Capability and Cell Toxicity of Compounds of Present Invention The IFN-γ production capability of the compounds of the present invention was investigated as follows. Moreover, with each compound of the present invention, a Aleurites fordii methanol extract (Total), a Daphne genkwa methanol extract (P10) of which anti-influenza virus activity has been reported (Korean Patent Application No. 10-2009-0034132), genkwadaphnin (GD), yuanhuacine (YH) and phorbol 12-myristate 13-acetate (PMA) were used as a positive control group. The Daphne genkwa methanol extract was obtained by adding 4 L of methanol to a total of 2 Kg of Daphne genkwa dry material collected in Yongin, Kyunggido, extracting the result for 24 hours while rotating at room temperature, collecting the filtered supernatant, and then concentrating the result under reduced pressure.

First, in order to detect IFN-γ, $2 \times 10^5$ NK92 cell/mL was inoculated in a 48-well culture plate, and was cultured for 12 hours with each of the compounds or extracts in an α-MEM medium containing 20% FBS and IL-2. The IFN-γ released in the culture supernatant was analyzed using an ELISA method. The absorbance was measured on a microplate reader and the treatment and the analysis for all the compounds or extracts were repeated twice. The cell toxicity of the compound-treated NK92 cells was evaluated through an MTT analysis.

The results are shown in FIG. 7 and FIG. 8.

As seen in FIG. 7 and FIG. 8, it was seen that Compounds 1 to 5 all induced the production of IFN-γ in NK92 cells. In addition, an effective dose of each compound for IFN-γ production significantly varied. FIG. 7 showed that Compounds 1, 3 and 4 (64 nM) had significant effects of 2 to 3 times or higher on the IFN-γ production compared to the same does of the Daphne genkwa methanol extract (P10). In addition, Compounds 2 (1.6 μM) and 5 (8 μM) also had activity for inducing IFN-γ production when applied to NK92 cells. FIG. 8 showed that Compound 1 of the present invention had high activity for inducing IFN-γ production even at a level of 40 nM, and Compound 3 and 4 (4 nM) had similar or higher activity for inducing IFN-γ production compared to the same dose of the phorbol 12-myristate 13-acetate (PMA). Based on these results, it was verified that the phorbol-type diterpene compounds isolated from the leaf of Aleurites fordii in the present invention are useful as an IFN-γ inducing agent.

The invention claimed is:
1. A compound represented by the following Chemical Formula 1 or a pharmaceutically acceptable salt thereof:

[Chemical Formula 1]

2. A method of enhancing production of interferon-gamma in a subject, comprising administering a composition to the subject, wherein the composition comprises a compound represented by Chemical Formulae 2 to 4 or a pharmaceutically acceptable salt thereof as an active ingredient:

[Chemical Formula 2]

[Chemical Formula 3]

[Chemical Formula 4]

wherein, in the formulae,
$R_1$ is $CH_2OH$ or $CH_3$; and
$R_2$ is $CH_3$ or $CH_2OH$.

3. The method according to claim 1, which enhances interferon gamma production in natural killer cells.

* * * * *

UNITED STATES PATENT AND TRADEMARK OFFICE
CERTIFICATE OF CORRECTION

PATENT NO. : 9,174,925 B2
APPLICATION NO. : 14/353892
DATED : November 3, 2015
INVENTOR(S) : Sei Ryang Oh et al.

It is certified that error appears in the above-identified patent and that said Letters Patent is hereby corrected as shown below:

In the claims,

At column 18, lines 49-50,

Change "3. The method according to claim 1, which enhances interferon gamma production in natural killer cells."

To -- 3. The method according to claim 2, which enhances interferon gamma production in natural killer cells. --

Signed and Sealed this
Sixteenth Day of February, 2016

Michelle K. Lee
*Director of the United States Patent and Trademark Office*